(12) United States Patent
Ando et al.

(10) Patent No.: US 10,360,814 B2
(45) Date of Patent: Jul. 23, 2019

(54) MOTION LEARNING SUPPORT APPARATUS

(71) Applicant: JAPAN SCIENCE AND TECHNOLOGY AGENCY, Saitama (JP)

(72) Inventors: Hideyuki Ando, Osaka (JP); Taro Maeda, Osaka (JP); Daisuke Kondo, Osaka (JP); Kazutaka Obama, Kyoto (JP); Hiroyuki Izuka, Hokkaido (JP)

(73) Assignee: Japan Science and Technology Agency (JP)

( * ) Notice: Subject to any disclaimer, the term of this patent is extended or adjusted under 35 U.S.C. 154(b) by 96 days.

(21) Appl. No.: 15/104,385

(22) PCT Filed: Dec. 26, 2013

(86) PCT No.: PCT/JP2013/084957
§ 371 (c)(1),
(2) Date: Jun. 14, 2016

(87) PCT Pub. No.: WO2015/097825
PCT Pub. Date: Jul. 2, 2015

(65) Prior Publication Data
US 2016/0314713 A1    Oct. 27, 2016

(51) Int. Cl.
*G09B 23/28*    (2006.01)
*G09B 5/02*    (2006.01)
(Continued)

(52) U.S. Cl.
CPC ............. *G09B 23/285* (2013.01); *G09B 5/02* (2013.01); *A61B 5/1124* (2013.01); *A61B 5/16* (2013.01);
(Continued)

(58) Field of Classification Search
CPC ......... A61B 5/16; A61B 5/1124; A61B 5/162; A61B 5/4082; G06T 11/203;
(Continued)

(56) References Cited

U.S. PATENT DOCUMENTS 5,904,484 A * 5/1999 Burns ................ A63B 24/0003
434/252
5,984,684 A * 11/1999 Brostedt ............ A63B 24/0003
434/247

(Continued)

FOREIGN PATENT DOCUMENTS

JP    8-182786    7/1996
JP    10-274918    10/1998
(Continued)

OTHER PUBLICATIONS

Saori Ota et al.; "Design and Development of a Learning Support Environment for Apple Peeling by Data Gloves", IEICE Technical Report, Mar. 3, 2012, (Mar. 3, 2012), vol. 111, No. 473, pp. 155 to 160.

(Continued)

*Primary Examiner* — Jack Yip
(74) *Attorney, Agent, or Firm* — Jordan and Koda, PLLC

(57) ABSTRACT

A motion learning support apparatus displays a teaching-aid video segment and a segment of practice video of a learner alternately on a monitor, the practice video being of the learner who is imitating a motion of the teaching-aid video segment and being taken with an imaging unit. The motion learning support apparatus includes: motion detection unit to detect a motion of the learner and a motion information acquisition unit; an evaluation unit to evaluate similarity of a motion of the learner to a motion in the teaching-aid video segment; and first learning support processing unit to, when the evaluation unit evaluates that the motions are similar, switch the monitor from video taken with the imaging unit (Continued)

to a following teaching-aid video segment. Thereby, vividness of an image due to the illusion effect induced to the learner can be improved, and so the learning effect can be improved for supporting.

5 Claims, 12 Drawing Sheets

(51) Int. Cl.

| | | |
|---|---|---|
| G06F 3/0488 | (2013.01) | |
| G06T 11/20 | (2006.01) | |
| A61B 5/16 | (2006.01) | |
| G09B 11/04 | (2006.01) | |
| A61B 5/11 | (2006.01) | |
| A61B 5/00 | (2006.01) | |
| G09B 15/00 | (2006.01) | |
| A63B 71/06 | (2006.01) | |

(52) U.S. Cl.
CPC ............ *A61B 5/162* (2013.01); *A61B 5/4082* (2013.01); *A63B 71/06* (2013.01); *G06F 3/04883* (2013.01); *G06T 11/203* (2013.01); *G09B 11/04* (2013.01); *G09B 15/00* (2013.01)

(58) Field of Classification Search
CPC ..... G06F 3/04883; G09B 11/04; G09B 15/00; G09B 23/286; G09B 5/02; A61L 35/16; A61L 5/1124; A61L 5/162; A61L 5/4082; A63B 71/06
USPC ........................................................ 434/262
See application file for complete search history.

(56) References Cited

U.S. PATENT DOCUMENTS

| 6,514,081 | B1* | 2/2003 | Mengoli | A63B 24/0003 |
| | | | | 434/252 |
| 2003/0054327 | A1* | 3/2003 | Evensen | A63B 24/0003 |
| | | | | 434/252 |
| 2008/0145830 | A1* | 6/2008 | Huang | G09B 9/00 |
| | | | | 434/336 |
| 2012/0206566 | A1* | 8/2012 | Fedoseyeva | G06Q 10/06398 |
| | | | | 348/38 |
| 2013/0071823 | A1* | 3/2013 | Lin | G09B 19/003 |
| | | | | 434/247 |
| 2014/0308640 | A1* | 10/2014 | Forman | G09B 19/003 |
| | | | | 434/258 |

FOREIGN PATENT DOCUMENTS

| JP | 10-309335 | 11/1998 |
| JP | 2000-504854 | 4/2000 |
| JP | 2007-323268 | 12/2007 |
| WO | WO- 97/29814 | 8/1997 |
| WO | WO- 2012/060901 | 5/2012 |

OTHER PUBLICATIONS

Dan Mikami et al., "A Video Feedback System Providing Motions Synchronized with Reference Examples for Motor Learning", Kenkyu Hokoku Consumer Device & System (CDS), [online], Sep. 5, 2013 (Sep. 5, 2013), 2013-CDS-vol. 8, No. 3, [retrieval date Mar. 20, 2013 (Mar. 20, 2013)], Internet <URL:https://ipsj.ixsq.nii.ac.jp/ej/?action=repository_action_comoon_download&item_id=9513&item_no=1&attributre_id=1&file_no=i>.

Kenta Matsuyoshi et al., "Kaigo * Kango Gaknshu ni Okern Doga Hikaku Kyozai o Mochiita Gakushu Shien System no Kochiku (O)", Dai 2 Kai Forum on Data Engineering and Information Management—DEIM 2010—Ronbunshu, [online], May 25, 2010 (May 25, 2010), [retrieval date Mar. 20, 2013 (Mar. 20, 2013)], Internet <URL:http//db-event.jpn.org/deim2010/proceedings/files/F8-1.pdf>.

Daisuke Kondo, Hiroyuki Iizuka, Hideyuki Ando, Kazutaka Obama, Yoshiharu Sakai, Taro Maeda, "Learning support using self-other motion overlapping for laparoscopy training", No. 13-2 Proceedings of the 2013 JSME Conference on Robotics and Mechatronics, Tsukuba, Japan, May 22-25, 2013.

Koji Ikuta, Junya Fukuyama, Akira Nakanishi, Koji Hotta, "Study on portable virtual endoscope with force sensation—Development of the record and reproduce system of insertion skill and the fixed-quantity rating method of the insertion skill-", 1P1-2F-D4, [No. 03-4] Proceedings of the 03' Japan Society of Mechanical Engineers Conference on Robotics and Mechatronics.

Henry Lin et al: "Towards automatic skill evaluation: Detection and segmentation of robot-assisted surgical motions", Computer Aided Surgery, vol. 11, No. 5, Sep. 1, 2006 (Sep. 1, 2006), pp. 220-230, XP055147790, ISSN: 1092-9088, DOI: 10.1080/10929080600989189 The Whole Document.

* cited by examiner

MOTION LEARNING SUPPORT APPARATUS

TECHNICAL FIELD

The present invention relates to a motion learning support apparatus for motion learning through teaching-aid video on the motion, such as for training of laparoscopic surgery, and relates to such a method for supporting motion learning.

BACKGROUND OF THE INVENTION

Laparoscopic surgery not requiring an incision during surgery of organs, for example, has the advantages to the patient that burden on the patient is lightened and recovery times are shorter, and so is expected to be commonly performed because of its effectiveness especially for elderly or children who are insufficient in strength. The laparoscopic surgery, however, requires a high level of skill, and the number of specialists is not enough, and so training an expert is an important issue. Conventionally as a training method for that, a training method using a dry box has been proposed. This training method, however, is just simulation of operations, and when an expert tells a non-expert about the skill, they show the skill while pointing a monitor screen with their fingers or verbally tell the skill in most cases, and a non-expert often performs dry-box training through trial and error while not fully understanding of the "knack" of the expert's skill.

Patent Literature 1 describes a technique of displaying a target image 11, which is taken with a TV camera beforehand and is stored in a digital memory, in the foreground (front side) of a TV monitor, while displaying an image 12 of a trainee in the background (back side) on the same monitor, whereby both of the motions are compared visually.

Patent Literature 2 describes a motion learning device configured to generate an image of a teacher's motion in the same frame of reference as that of a student, thus providing a more effective method of learning. Specifically the device includes a host computer 12, a monitor 10, a motion sensing device 15 and a sensor 20, and at a first step for training, a motion sequence is acquired from a teacher, and a virtual image of the trajectory of the student's imitating motion is displayed on the monitor 10 alongside the trajectory of the teacher's motion. The literature also mentions that, as the student's ability to imitate the teacher improves, the computer 12 automatically increases the speed of the teacher's motion to increase the difficulty.

Non-Patent Literature 1 describes a laparoscopic-surgery training device configured to divide teaching-aid video into segments of motion in about ten seconds, enabling a learner to perform partial learning. This device is to reproduce one segment of the image on a monitor firstly, and every time the segment ends, the video is switched into the one of the forceps held by the learner to urge the learner to replicate the motion in the range shown to the learner this time. During this, the final frame of the model video is displayed in a semitransparent and overlapped manner for 0.5 sec and every 1.2 seconds. Then, when the learner thinks that their forceps assume the target posture, the learner manipulates a foot pedal to progress the video to the next motion segment, and then the following model video starts to be reproduced from the same posture. A subjective report can be obtained therefrom such that, when the image is switched between self and other images, the learner feels as if the forceps moved spontaneously to proceed to the following procedure.

Non-Patent Literature 2 describes a technique of additionally including a system to record and reproduce insertion skill of an expert physician on a time-series basis, so as to allow a learner to experience and learn such insertion skill of the expert physician. The literature further mentions that they developed a method for evaluating the insertion skill quantitatively and enabled more effective training by evaluating the skill of a trainee, and as a method therefor, (1) teaching (teaching a model insertion skill using the recording/reproducing system), (2) trial (insertion of an endoscope), and (3) evaluation (providing evaluation values obtained through the insertion) are proposed.

CITATION LIST

Patent Literature 1: Patent Application Publication No. H08-182786
Patent Literature 2: Patent Application Publication No. 2000-504854
Non-Patent Literature 1: Daisuke KONDO, Hiroyuki IIZUKA, Hideyuki ANDO, Kazutaka OBAMA, Yoshiharu SAKAI, Taro MAEDA, "Learning support using self-other motion overlapping for laparoscopy training", No. 13-2 Proceedings of the 2013 JSME Conference on Robotics and Mechatronics, Tsukuba, Japan, May 22-25, 2013
Non-Patent Literature 2: Koji IKUTA, Junya FUKUYAMA, Akira NAKANISHI, Koji HOTTA, "Study on portable virtual endoscope system with force sensation-Development of the record and reproduce system of insertion skill and the fixed-quantity rating method of the insertion skill-", 1P1-2F-D4, [No. 03-4]Proceedings of the 03' Japan Society of Mechanical Engineers Conference on Robotics and Mechatronics

SUMMARY OF THE INVENTION

Patent Literatures 1, 2 and Non-Patent Literature 2 are not configured to divide a series of motion into a plurality of segments, and to display them and the self-images alternately on a monitor during the course of the learning. Therefore these literatures do not describe the relationship between evaluations of a segment and shifting to the next segment at all.

Non-Patent Literature 1 simply describes the device that is configured to progress the teaching-aid video to the following motion segment when the learner manipulates the pedal, and does not describe another method to change the segment of the motion of a teaching-aid video.

The present invention aims to improve the vividness of an image obtained from the illusion effect that occurs when the motion of a learner is close to the motion of the teaching-aid video segment, and to this end, to switch the video into the next teaching-aid video segment automatically, thus improving the learning effect for supporting.

A motion learning support apparatus according to the present invention includes: a first learning support processor configured to display a teaching-aid video segment and a segment of practice video of a learner alternately on a monitor, the teaching-aid video segment being obtained by dividing teaching-aid video on a motion in a time direction, and the practice video being of the learner who is imitating a motion of the teaching-aid video segment and being taken with an imaging unit; a motion sensor configured to detect a motion of the learner; and an evaluation unit configured to evaluate similarity of a motion of the learner to a motion in the teaching-aid video segment, and the first learning support processor is configured to, when the evaluation unit evaluates that the motions are similar, switch the monitor from video taken with the imaging unit to a following teaching-aid video segment.

A method for supporting motion learning according to the present invention includes: a display step of displaying a teaching-aid video segment and a segment of practice video of a learner alternately on a monitor, the teaching-aid video segment being obtained by dividing teaching-aid video on a motion in a time direction, and the practice video being of the learner who is imitating a motion of the teaching-aid video segment and being taken with an imaging unit: an evaluation step of detecting a motion of the learner in the display step and evaluating similarity of a motion of the learner to a motion in the teaching-aid video segment; and a switching step of, when it is evaluated that the motions are similar, switching the monitor from video taken with the imaging unit to a following teaching-aid video segment.

According to these aspects of the invention, a motion of the learner is detected, and thereby similarity of a motion of the learner to a motion in the teaching-aid video segment is evaluated. When it is evaluated that the motions are similar, the monitor is switched from video taken with the imaging unit to a following teaching-aid video segment. With this configuration, if the motion of the learner is similar to the motion in the teaching-aid video segment, i.e., if they are brought closer, the video is switched in a timely manner so that the motion in the video of the learner can lead to the following teaching-aid video segment, whereby the learner has an illusion as if they started a motion of the next segment similarly to that of the model person, and can have a memory thereof as a more vivid and specific behavior image, so that the learning effect therefrom can be more improved.

According to the present invention, a teaching-aid video segment is automatically progressed to the next segment, whereby vividness of an image due to the illusion effect induced to the learner can be improved, and so the learning effect can be improved.

BRIEF DESCRIPTION OF THE DRAWINGS

FIG. 3A shows a video frame showing changing in the manner of holding a needle, FIG. 3B shows a video frame showing inserting a needle, and FIG. 3C shows a video frame showing winding suture thread.

DESCRIPTION OF THE PREFERRED EMBODIMENTS

Figure 1:
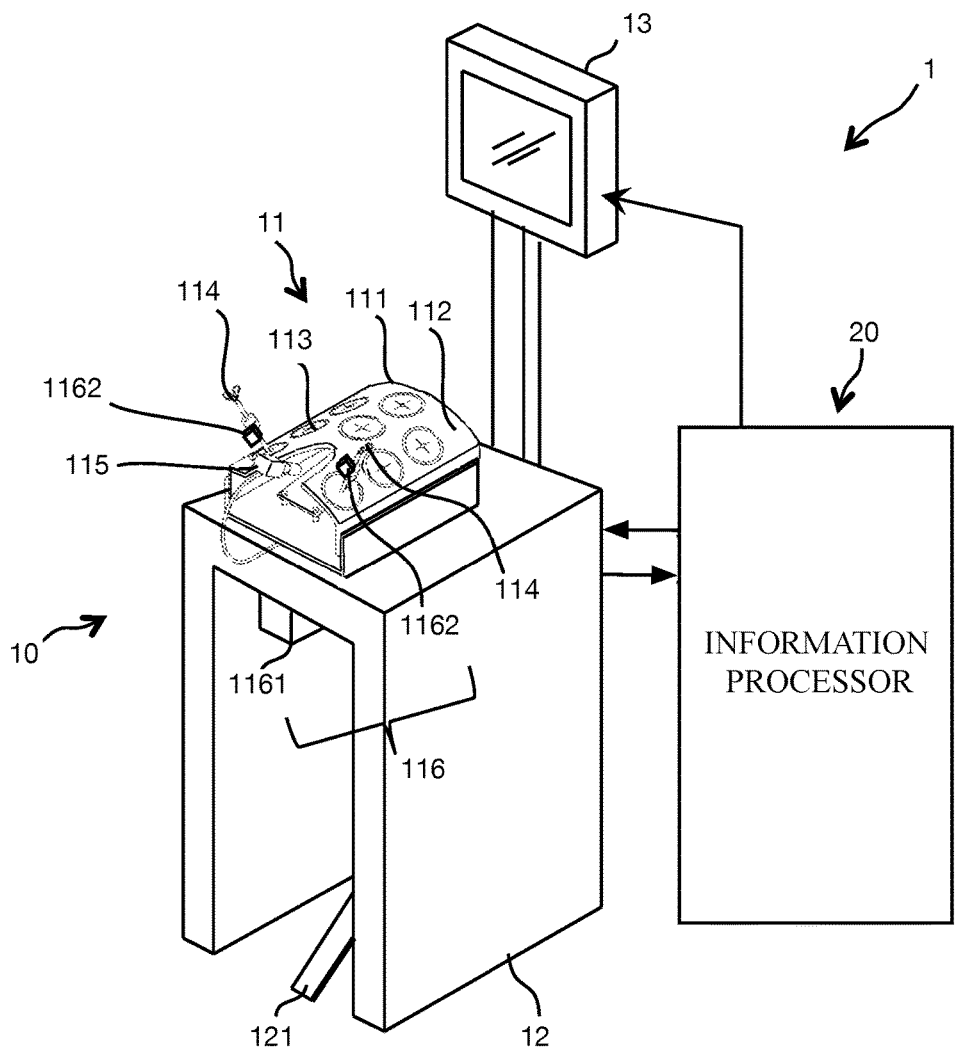
FIG. 1 schematically shows the configuration of a motion learning support apparatus that is one embodiment according to the present invention.

FIG. 1 schematically shows the configuration of a motion learning support apparatus that is one embodiment according to the present invention. A motion learning support apparatus 1 is applicable to devices for learning of various motions. The following describes the motion learning support apparatus 1 specifically, by way of an apparatus used to support motion learning (practicing) of suture ligature using forceps during laparoscopic surgery.

In FIG. 1, the motion learning support apparatus 1 includes a device for practicing 10 and an information processor 20. The device for practicing 10 includes a dry box 11 that imitates a patient's body, a base 12 on a predetermined position of which the dry box 11 is to be placed, and a monitor 13 to display video. The dry box 11 has a tubular body 111 placed sideways to have a flat bottom face. The tubular body 111 has an upper-face 112 that is a convex curved face so as to imitate an abdomen of a human body. The upper-face 112 is made of a transparent or semitransparent member, in which a plurality of circle holes is formed at appropriate positions. At each of these circle holes, a film member 113 made of resin, for example, is attached, at a center of which a cross-shaped cutting is formed, the cutting imitating a cylindrical trocar in terms of its function, through which forceps or an endoscopic camera described later is to be inserted or removed. In another embodiment, a structure imitating a trocar may be directly disposed.

Forceps 114 are inserted through the cross-shaped cutting at the film member 113 from the above. As is well known, the forceps 114 for ligature, for example, have a pair of finger insertion parts on the proximal side and a pair of openable/closable action parts (a pair of pinching members) on the other side, where the both sides are jointed with a pipe of a predetermined length. The pipe is internally provided with a mechanism to transmit the operating force at the finger insertion parts to the action parts. Such a force transmission mechanism allows the pair of action parts on the forward end to operate in association with the opening/closing operation by a user through the finger insertion parts, whereby a target can be pinched or released accordingly. The forceps 114 are configured to, by opening the action parts, assume the posture enabling introduction of a needle or suture thread described later into the pair of action parts, followed by closing the pair of action parts so as to pinch the needle or the suture thread therebetween.

A not-illustrated dummy diseased part made of a resin member, for example, is disposed inside of the dry box 11. The dummy diseased part is a rectangular parallelopiped shaped object, on an upper face of which a dummy incision part is formed to allow for suturing. The film member 113 in the present embodiment is to insert and remove the forceps 114 only, and the endoscopic camera 115 is fixedly provided at an appropriate place of the dry box 11. The endoscopic camera 115 is to present the space for procedure to a learner in an observable manner, which is set in the direction so that the dummy diseased part is located at the center of the visual field and takes an image of the motion of the forward-end action parts of the forceps 114 during suture at the dummy diseased part.

The base 12 is provided with a foot pedal as one example of a manipulation unit 121 at an appropriate place thereof, e.g., at the bottom. As is well known, the manipulation unit 121 internally includes a swingable structure and a switch that turns ON in response to press-down operation.

The device for practicing 10 includes a motion sensing unit 116. The motion sensing unit 116 includes a magnetic generator 1161 and a magnetic sensor 1162. The magnetic generator 1161 is a source to generate magnetic signals, and is fixedly provided at an appropriate position of the base 12. The magnetic sensor 1162 is attached to a predetermined position of the forceps 114 so as to be directed in triaxial directions. The magnetic sensor 1162 detects magnetic signals corresponding to each of the triaxial directions and generated from the magnetic generator 1161, thus detecting the three-dimensional position and the direction. Based on the attached position and direction to the forceps 114 and the known shape and dimensions of the forceps 114, for example, the position and the posture (direction) of the forward-end action parts (part to be focused) of the forceps 114 are calculated based on the information detected by the motion sensing unit 116 by a motion information acquisition unit 215 described later. Instead of the magnetic motion sensing unit 116, a three-dimensional acceleration sensor may be used or an image taken with the endoscopic camera 115 may be analyzed to detect the position and the posture (direction) of the forward-end action parts of the forceps 114.

The monitor 13 in the present embodiment is attached to the base 12. The monitor 13 is disposed at a position where a learner can easily view during motion learning using the dry box 11, preferably behind the base 12 and at a position corresponding to the height of the learner's eyes.

The information processor 20 is to input/output information with respect to the device for practicing 10, and to create a motion teaching-aid as described later based on the input information and other information and send the teaching aid to the monitor 13.

Figure 2:
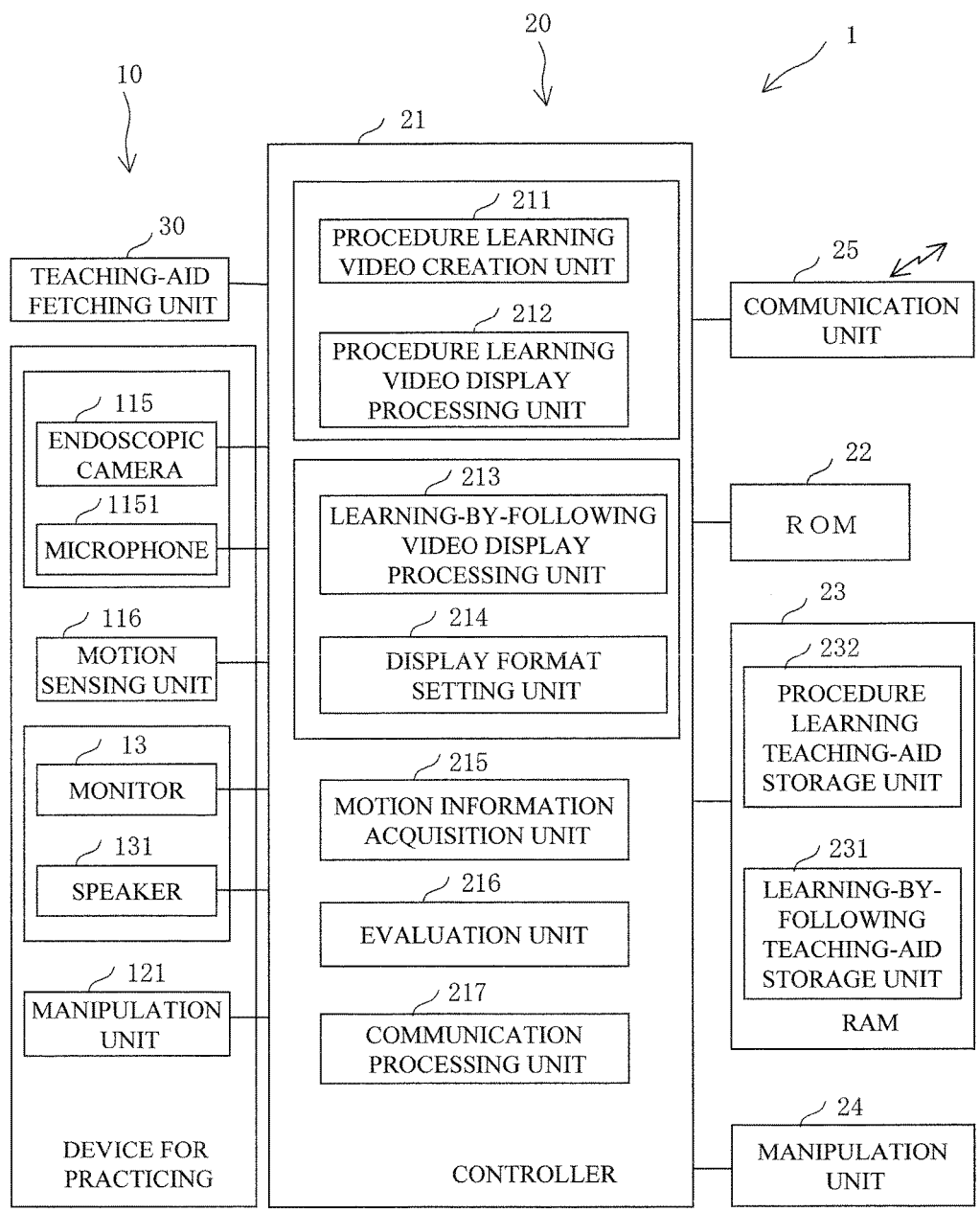
FIG. 2 shows a circuit configuration that is one embodiment of the motion learning support apparatus according to the present invention.

FIG. 2 shows a circuit configuration that is one embodiment of the motion learning support apparatus according to the present invention. In FIG. 2, the device for practicing 10 is provided with a microphone 1151 and a speaker 131. The microphone 1151 is to fetch, as sound information, the knack or guidance about motion of a person who performs a model motion when a teaching-aid is created. As described later, the speaker 131 is to reproduce the sound information acquired with the microphone 1151 during learning.

The information processor 20 includes a controller 21 made up of a CPU (Central Processing Unit), a ROM (Read Only Memory) 22, a RAM (Random Access Memory) 23, a manipulation unit 24, and a communication unit 25 provided as needed. The ROM 22, the RAM 23, the manipulation unit 24, and the communication unit 25 are connected to the controller 21. The ROM 22 stores required processing programs and information necessary to execute the programs beforehand, and the RAM 23 is to execute information processing as well as to temporarily store the processed information. The RAM 23 includes a learning-by-following teaching-aid storage unit 231 to store a series of video of a model motion, and a procedure learning teaching-aid storage unit 232 to store a segmented video of the teaching-aid obtained by dividing a series of video of a model motion into a video part of each motion element as described later.

The manipulation unit 24 is made up of a touch panel, a mouse, a keyboard or the like, to create a teaching-aid or to perform manipulation or instructions necessary to execute learning support processing. The communication unit 25 is connected to two motion learning support apparatus, one of which is for a model person and the other is for a learner, and is used to exchange video information mutually when live videos of both sides are to be synthesized for display (in the present embodiment, time-dividing display).

The information processor 20 functions, through execution of the processing programs stored at the ROM 22 by the CPU, as a procedure learning video creation unit 211, a procedure learning video display processing unit 212, a learning-by-following video display processing unit 213, a display format setting unit 214, a motion information acquisition unit 215, an evaluation unit 216, and a communication processing unit 217 provided as needed.

At the device for practicing 10, a model person performs a model motion for suture ligature beforehand, and the state of this model motion is acquired with the endoscopic camera 115 and the microphone 1151, and is stored in the learning-by-following teaching-aid storage unit 231 of the RAM 23. Alternatively, teaching-aid video (including sound as needed) about suture ligature procedure which is stored beforehand in an external recoding medium may be stored in the learning-by-following teaching-aid storage unit 231 via a teaching-aid fetching unit 30 or the communication unit 25. When teaching-aid video is acquired, the motion sensing unit 116 acquires information on the position and the direction of the forward-end action parts of the forceps 114 in the time-measuring direction successively as well, which is stored similarly to the teaching-aid video.

The procedure learning video creation unit 211 is to create procedure learning video (teaching-aid video) from video on suture ligature procedure by a model person. The procedure learning video creation unit 211 reproduces video on suture ligature procedure by a model person, and when a dividing condition happens, such as a scene where the motion of the forceps 114 substantially stops or where audio guide is interrupted during reproduction, the procedure learning video creation unit 211 determines it as a break of the motion element. Then, the procedure learning video creation unit 211 divides (cuts out) the video part before the break and assigns a procedure number, e.g., a serial number thereto. A teaching-aid video segment having a motion element corresponding to each time width divided is written into the procedure learning teaching-aid storage unit 232 in association with the procedure number successively. Herein, the determination whether the motion of the forceps 114 substantially stops or not during reproduction may be made by picking up the video on the forceps 114 from the video and based on the motion thereof in the video, or may be performed by the motion information acquisition unit 215 described later based on three-dimensional information obtained at the motion sensing unit 116. In another embodiment, it may be determined based on the motion of the forward-end action parts of the forceps 114. Instead of writing a teaching-aid video segment in the procedure learning teaching-aid storage unit 232, information (frame information) indicating the cutting-out position of each teaching-aid video segment may be written in another embodiment.

A series of motion with the forceps 114 (which may include the motion of a needle and suture thread) during suture ligature procedure includes a plurality of motion elements (an element corresponds to each procedure) in the time direction. For instance, they include (1) motion to change the manner of holding a needle with forceps (procedure number 1), (2) motion to insert a needle (procedure number 2), (3) motion to pull suture thread and make a letter C shape (procedure number 3), (4) motion to wind twice (procedure number 4) and (5) motion for ligature (procedure number 5).

Figure 3A:
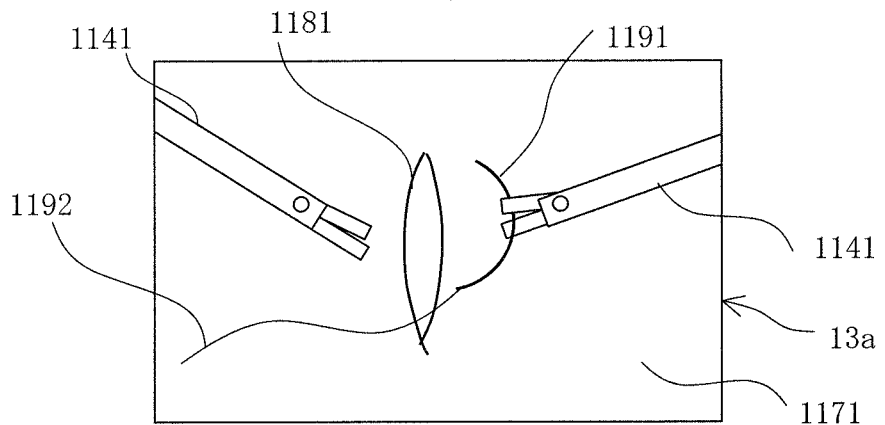
FIGS. 3A to 3C show one example of video frames in procedure learning, where
Figure 3B:
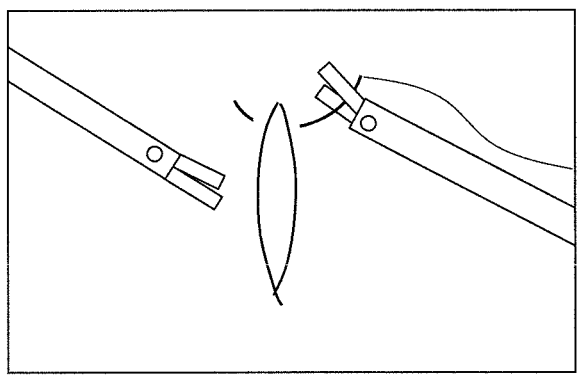
Figure 3C:
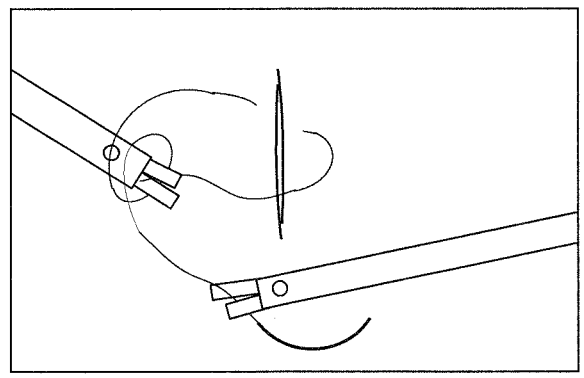

FIGS. 3A to 3C show one example for reference of video frames in procedure learning, where FIG. 3A shows a video frame corresponding to the procedure number 1 to change the manner of holding a needle, FIG. 3B shows a video frame corresponding to the procedure number 2 to insert a needle, and FIG. 3C shows a video frame corresponding to the procedure number 3 to wind suture thread. In FIGS. 3A to 3C, a monitor screen 13a shows video taken with the endoscopic camera 115, where the entire screen shows dummy diseased part video 1171 and an incision part video 1181 is displayed at a substantially center thereof. In the monitor screen 13a, forceps video 1141, needle video 1191 that is pinched at the forward-end action parts of the forceps 114, and suture thread video 1192 connected to one end of the needle video 1191 are displayed.

The procedure learning video display processing unit 212 shifts to a procedure learning video display mode in response to an instruction for procedure learning, and then reads out teaching-aid video segments in accordance with their assigned procedure numbers from the procedure learning teaching-aid storage unit 232 and displays them on the monitor 13. Thereby, a learner understands the learning point of a motion element in each procedure. Every time the reproduction of one teaching-aid video segment ends, the procedure learning video display processing unit 212 switches the monitor 13 to display the video of the endoscopic camera 115. Thereby, the learner can imitate the motion element in the teaching-aid video segment that the learner observed immediately before.

When the reproduction of one teaching-aid video segment ends, the procedure learning video display processing unit 212 displays a static image of the final video frame of the teaching-aid video segment reproduced immediately before, alongside the video taken with the endoscopic camera 13 (live video). Such alongside-displaying is preferably based on a view synthesis method. Thereby, the learner can easily understand the final reaching position of the forceps 114 in the segment.

Figure 4:
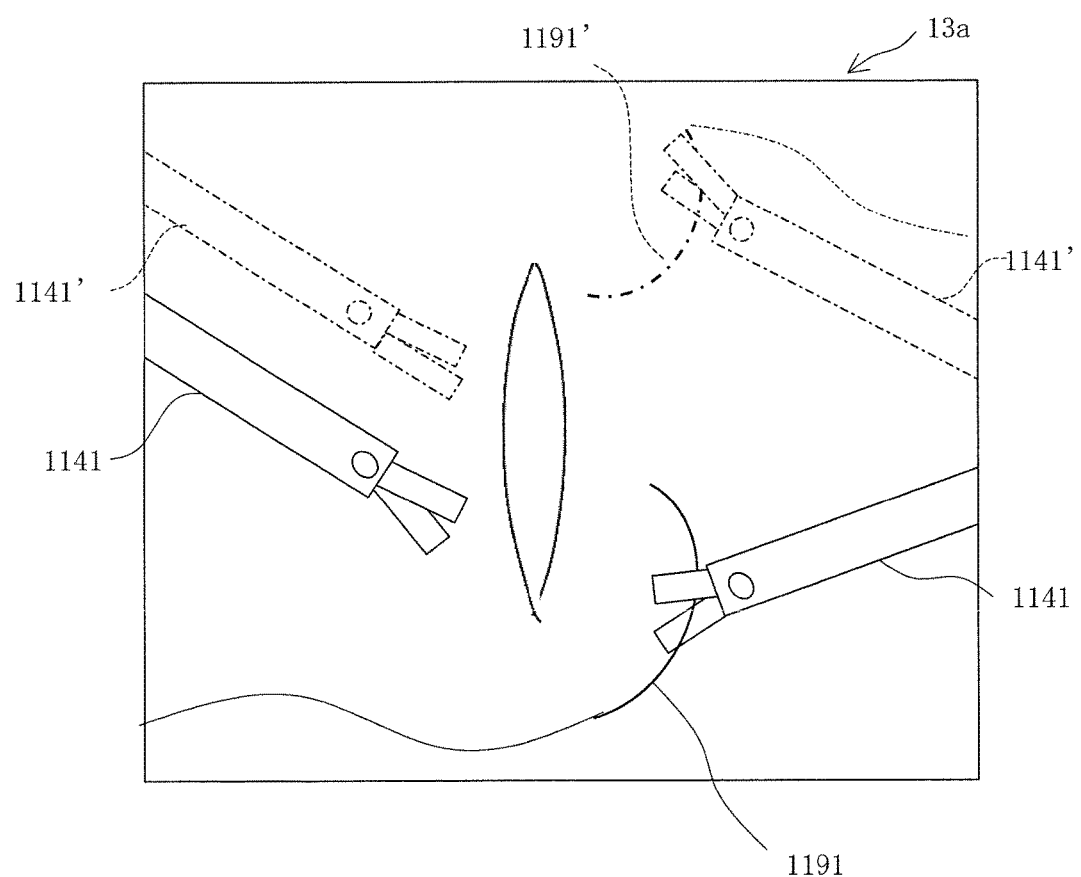
FIG. 4 shows one example of the alongside-displaying.

FIG. 4 shows one example of the alongside-displaying. In this drawing, parts indicated with solid lines are an example of practice video that is taken with the endoscopic camera 115 (live), and parts indicated with dot-and-dash lines are an example of static image at the end of the same teaching-aid video segment.

In the example of FIG. 4, the practice video shows the state during the procedure number (1), and the dot-and-dash line parts are a static image at the end (in this case, the final frame) of the procedure number (1). Therefore the learner tries to manipulate through the practice video of its own to move the image 1141 of the forceps 114 to static image 1141' as the final reaching position.

The alongside-displaying is preferably by displaying noticeably the forceps video 1141' of the model person only. Such forceps video 1141' may be picked up by taking an image of the model video while applying light to the forceps 114 using illumination light, and by setting a threshold in the brightness to the final video frame. Alternatively, a specific color may be given to the forceps 114, for example, and the forceps video 1141' may be extracted based on a difference in color. In the present embodiment, the final video frame is displayed by blinking at a predetermined frequency, e.g., at a tenth of a few Hz to a few Hz, and at 1 Hz in this example, whereby distinguishing from the video taken with the endoscopic camera 115 becomes easy. Such display by blinking can be implemented by displaying the final video frame at every predetermined time on the monitor 13.

The procedure learning video display processing unit 212 differently switches the display from the video taken with the endoscopic camera 115 to the next teaching-aid video segment in accordance with evaluations by the motion information acquisition unit 215 and the evaluation unit 216 described later. When evaluation by the evaluation unit 216 is good, the procedure learning video display processing unit 212 automatically switches the video displayed on the monitor 13 to the following teaching-aid video segment. This is because, in the view synthesis method, when a learner brings the video 1141 of the manipulated forceps 114 to a position overlapped with the forceps video 1141', if the video can be switched in a timely manner so that the motion in the video 1141 of the forceps 114 can lead to the following teaching-aid video segment, the learner have an illusion as if the learner started a motion of the next segment similarly to that of the model person, and can have a memory thereof as a more vivid and specific behavior image, so that the learning effect therefrom can be more improved. A method for the evaluation is described later.

On the contrary, when the evaluation is not good, the procedure learning video display processing unit 212 does not switch automatically, but receives a signal from the manipulation unit 121 as a foot pedal so as to perform switching to the next teaching-aid video segment. That is, when the evaluation is not good, and when the procedure number does not reach the final number, the procedure learning video display processing unit 212 switches the monitor 13 every time the learner operates the manipulation unit 121, and reads the next teaching-aid video segment from the procedure learning teaching-aid storage unit 232 to display it on the monitor 13. When the procedure number is the final, the procedure learning video display processing unit 212 performs repeat processing to return to the first procedure number. When the manipulation of the manipulation unit 121 is performed in a different manner, e.g., when it is pressed in a different manner such as pressing twice, or pressing for a long or short time, such manipulation maybe dealt with as an instruction to replay the same teaching-aid video segment for display, or to end the procedure learning video display mode. Alternatively, another manipulation member may be provided.

The learning-by-following video display processing unit 213 shifts to a learning-by-following video display mode in response to an instruction for learning-by-following, and thereby displays a series of teaching-aid video at the learning-by-following teaching-aid storage unit 231 and the practice video taken with the endoscopic camera 115 on the monitor 13 in a synthesized manner, and displays in an alternate time-dividing manner in this case.

Figure 5:
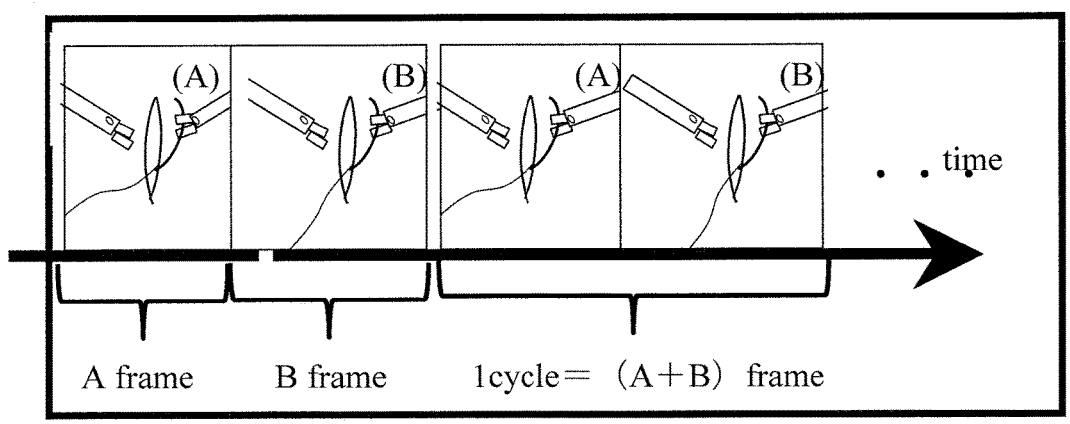
FIG. 5 schematically shows a time-dividing display of teaching-aid video (A) and live-video (B) of a learner.

FIG. 5 schematically shows a part of this display mode. In FIG. 5, (A) shows frames of a series of teaching-aid video at the learning-by-following teaching-aid storage unit 231, and (B) shows frames of the practice video taken with the endoscopic camera 115. On the monitor 13, these videos are rewritten at the frame period of 16.7 ms (1/60 Hz), for example. FIG. 5 showing this embodiment indicates that these videos are displayed while switching alternately, in which video (A) that is continuous in the time direction is displayed for time corresponding to the number of A frames, and video (B) that is continuous in the time direction is displayed for time corresponding to the number of B frames.

Therefore display period (one cycle) is time corresponding to the number of (A+B) frames, and the self-other (learner/model person) ratio is (B/A).

The display format setting unit 214 enables changing and setting of at least one of the display period and the self/other ratio in the learning-by-following video display mode via the manipulation unit 24.

The learning-by-following video display processing unit 213 in the present embodiment is based on a time-dividing display method to synthesize videos, which may be an overlapping method in which both of the videos are overlapped, or a parallel displaying method in which they are displayed together in parallel for some purposes. It should be noted that, in the case of applying the device to laparoscopic surgery training, there may be a case in the view overlapping presentation, followability may deteriorate when following the motion of forceps having a complicated overlapping with a small displacement. In this case, it is considered that since it requires matching between a lot of characteristic points, the followability deteriorates because of troublesome switching of the learner's attention between videos of the learner and the videos of the model person. Then, as a method for enabling following without shifting the attention, a time-dividing method is rather preferable, in which videos are switched alternately. Thereby, an illusion phenomenon is expected to occur at the learner, where the learner can feel like blending with the model person while keeping the feeling of integration with the model person. That is, the time-dividing method can induce, during a mutually cooperative physical motion, a motion where the learner does not lose the voluntariness of the self-motion and performs a motion naturally to follow the other person's motion because the videos including the self-video and the teaching-aid video from the same perspective are alternately switched on the monitor 13. Then, when following the motion in the teaching-aid video, the learner can feel the illusion as if blended motion parts on both sides that are displayed successively in the view were the one and self-motion part, i.e., blending feeling can be brought (generated). The blending feeling refers to a feeling such that the motion part on the learner side moves spontaneously or moves as the learner intends, i.e., voluntariness and involuntariness are blended. In other words, the learner can have a subjective feeling such that the motion part in the teaching-aid video seems not as the other person's motion part but nothing except for its own motion part. As a result, the learner presumably can execute matching of multiple points and the following motion under the consciousness such that the learner does not or cannot recognize the following error clearly.

The present applicant shows in the prior application (patent application No. 2012-97328) that, when self-motion video and following-target video taken from the same perspective are displayed in a time-dividing manner on a monitor, a preferable period to produce the above-mentioned effect is about 2 Hz to 4 Hz in terms of the frequency and such a self-other ratio is 1:1 to 1:3. Under this condition, the followability can be higher due to the blending feeling as stated above.

The motion information acquisition unit 215 calculates motion information of the forward-end action parts of the forceps 114 based on sensor data from the motion sensing unit 116 as stated above with a predetermined period, e.g., with a frame period (motion information includes parameters, such as the position, the direction and the displacement speed, as well as the displacement acceleration. Each parameter is a vector. The speed and acceleration are obtained based on sensor data at plurality of timings).

The evaluation unit 216 evaluates the skill of the learner about their forceps manipulation based on a difference or the like between motion information of the forceps 114 in the teaching-aid video obtained beforehand and the motion information on the forward-end action parts of the forceps 114 of the learner obtained by the motion information acquisition unit 215. The evaluation unit 216 further determines, based on the evaluation result, whether or not to automatically switch the display on the monitor 13 from the practice video to the next teaching-aid video segment. The determination result is output to the procedure learning video display processing unit 212 to issue an instruction as to whether or not to perform automatic switching.

Whether or not to perform automatic switching can be determined by various methods. For instance, all of the parameters of the motion information as stated above may be used in accordance with the purpose or the required precision. Alternatively, position information only may be used, position and direction information may be used, or position, direction and displacement speed information may be used.

In the present embodiment, the evaluation is made in two stages. Specifically at a first stage as the former stage, a variation state of a difference or the like in the parameters of the motion information between the learner and the model person is monitored, thereby determining whether the manipulation of the forceps by the learner approaches or not the motion corresponding to the motion at the end of the teaching-aid video in the current segment. At the second stage of evaluation, after affirming the determination at the check stage, prediction (evaluation) is made whether the motion of the learner naturally leads to the motion of the model person (i.e., the motions of the both persons are similar in the position, direction, displacement speed and displacement acceleration) by switching to the next teaching-aid video segment based on a difference in parameters of the motion information between both persons as well as based on a function indicating the skill based on the parameters, e.g., a function to calculate the norm for variance evaluation. Herein displacement acceleration is used for more correct evaluation on the forceps 114 manipulated by the learner in the current segment as to whether illusion for the behavior of the forceps 114 at the time of starting in the next segment occurs or not as if the learner started the motion in the next segment that is similar to the motion of the model person. Instead of using the displacement acceleration, evaluation may be made simply with the displacement speed.

Figure 6:
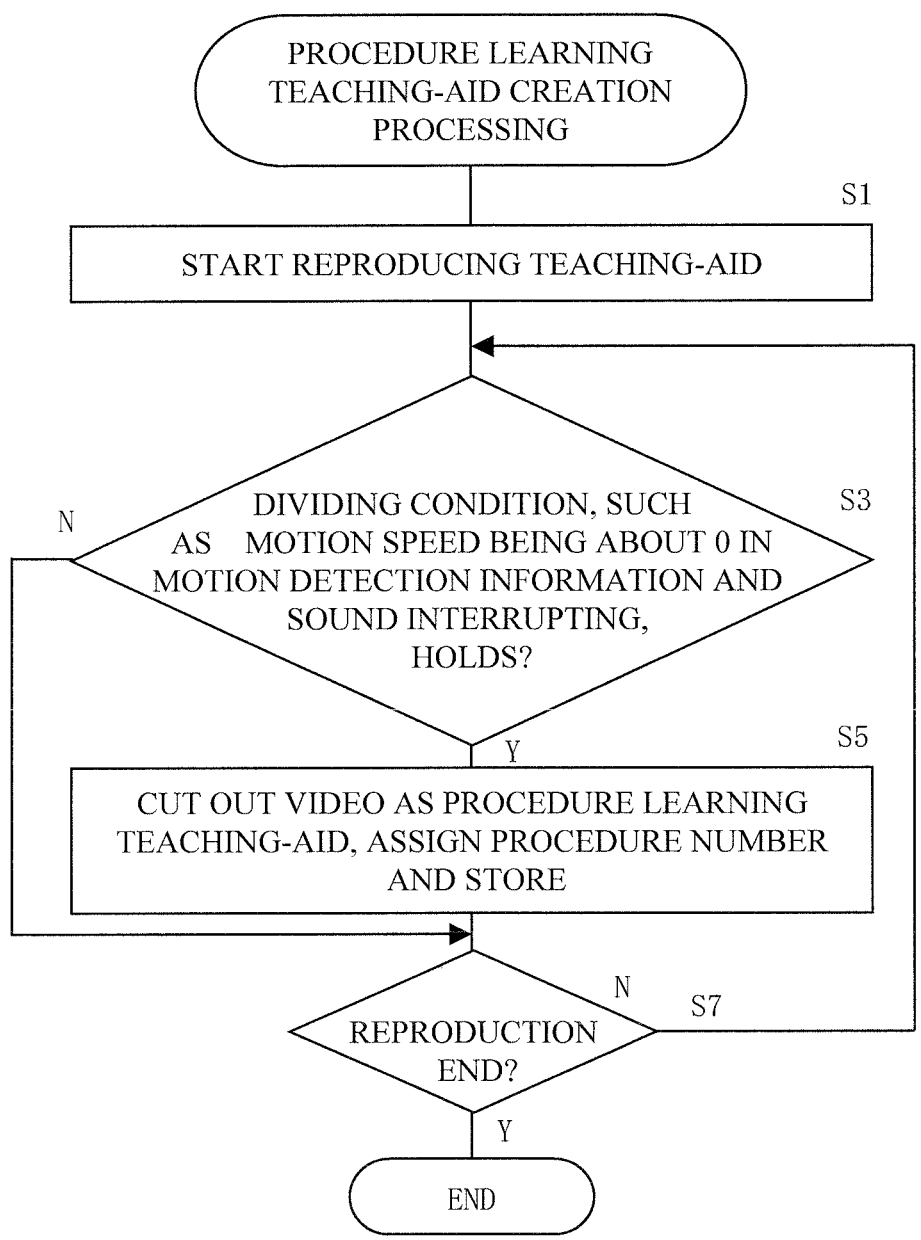
FIG. 6 is a flowchart showing one embodiment of the procedure learning teaching-aid creation processing.

FIG. 6 is a flowchart showing one embodiment of the procedure learning teaching-aid creation processing. Firstly an original teaching-aid performed by a model person starts to be reproduced (Step S1). Next, determination is made whether at least one of the conditions of motion speed being 0 (including substantially zero) in the motion detection information and of the sound interrupting holds or not as the dividing condition during reproduction (Step S3). If the dividing condition holds, the video from the beginning to the present or the video from the immediately preceding dividing position to the present when the dividing condition holds in the first procedure or later is cut out, to which a procedure number that is a serial number is assigned, and the video is stored in the procedure learning teaching-aid storage unit 232 (Step S5). The video may be actually cut out and may be stored individually in one embodiment, or information on the dividing position (stored address) may be associated with the procedure number for recording in another embodiment, whereby similar dividing processing is enabled by managing their addresses. Next, determination is made whether reproduction ends or not (Step S7). If it ends, this flow ends.

On the contrary, if no dividing condition holds at Step S3, the procedure proceeds to Step S7. Then unless the reproduction ends, the procedure returns to Step S3, and similar cutting-out processing is repeated.

Figure 7:
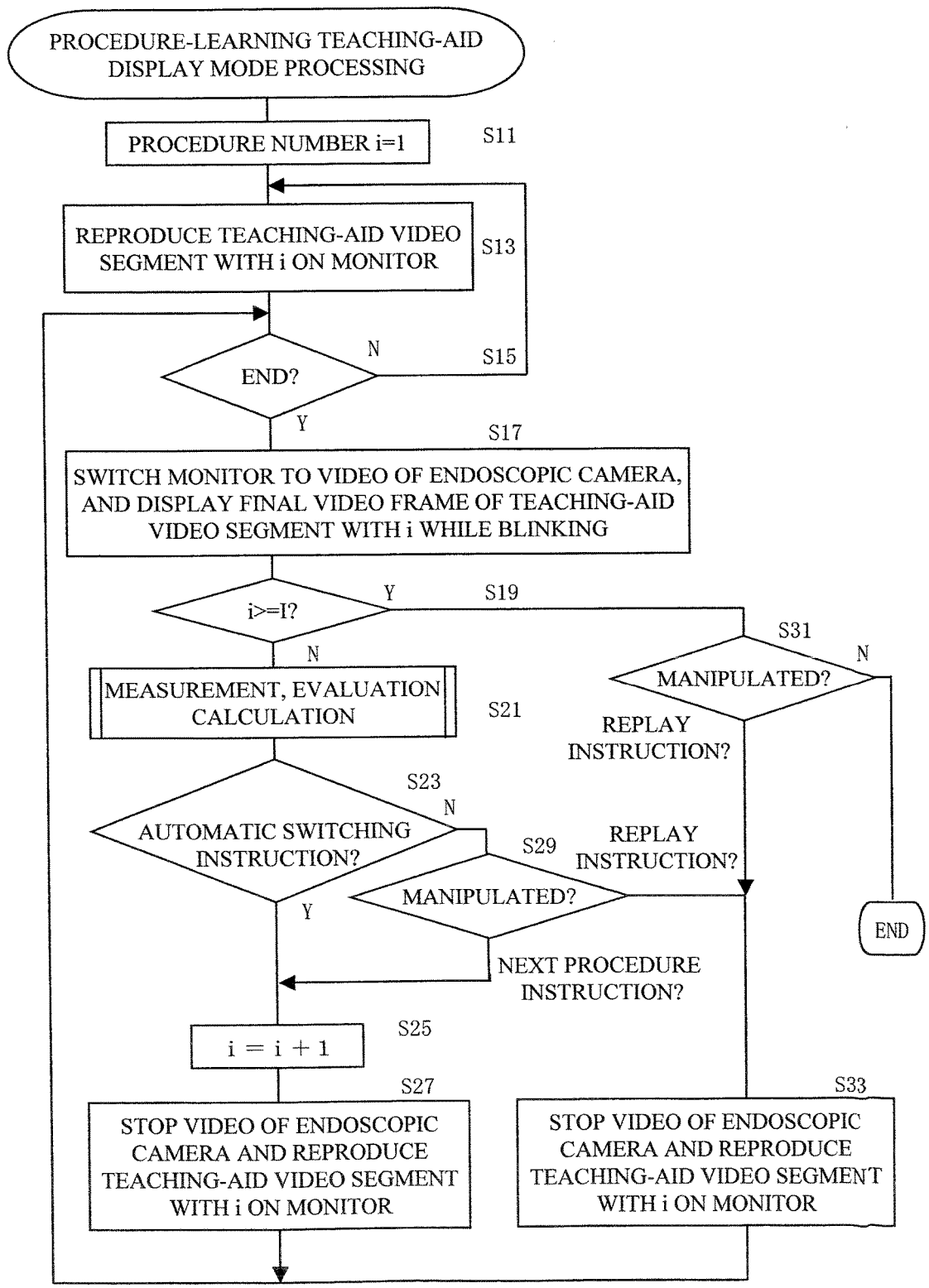
FIG. 7 is a flowchart showing one embodiment of the procedure learning teaching-aid display mode processing.

FIG. 7 is a flowchart showing one embodiment of the procedure learning teaching-aid display mode processing. Firstly i indicating the procedure number is set as i=1 (Step S11). Next, a teaching-aid video segment corresponding to the procedure number i is read out from the procedure learning teaching-aid storage unit 232 and is displayed (reproduced) on the monitor 13 (Step S13). After reading this teaching-aid video segment with the procedure number i, determination is made whether reading of the teaching-aid video segment ends or not (reproduction ends or not) (Step S15). If reading of the teaching-aid video segment does not end (during reproduction), the procedure returns to Step S13. If reading of the teaching-aid video segment ends, the display on the monitor 13 is switched to the live video taken with the endoscopic camera 115, and the final video frame of the teaching-aid video segment with the procedure number i is displayed alongside while blinking (Step S17).

Subsequently, determination is made whether the procedure number i is the final (procedure number I) or not (Step S19), and if it is the final, the procedure proceeds to Step S31. If it is not the final, measurement and evaluation calculation processing is executed (Step S21). The measurement and evaluation calculation processing is described later.

As a result of the measurement and evaluation calculation processing, determination is made whether an instruction of automatic switching is output or not (Step S23), and if an instruction of automatic switching is output, the procedure number i is incremented by 1 (Step S25), displaying of the video taken with the endoscopic camera 115 stops, and a teaching-aid video segment with the procedure number i after the increment is reproduced on the monitor 13 (Step S27).

On the contrary, if an instruction to inhibit automatic switching is output at Step S23, determination is made whether the manipulation unit 121 is manipulated or not (Step S29). Herein, if it is determined that manipulation is performed for instruction of the next procedure, the procedure number i is incremented by 1 (Step S25), displaying of the video taken with the endoscopic camera 115 stops, and a teaching-aid video segment with the procedure number i after the increment is reproduced on the monitor 13 (Step S27). Meanwhile, if it is determined that manipulation is performed for instruction of replay at Step S29, the teaching-aid video segment with the same procedure number i is reproduced again on the monitor 13 (Step S33).

At Step S19, if the procedure number i is the final, determination is made whether the manipulation is performed or not for instruction of replay (Step S31). If such a replay instruction is issued, the procedure proceeds to Step S33. If no instruction is issued in a predetermined time, it is regarded as ending of the procedure learning, and the present flow ends. Although not illustrated, the procedure may be configured capable of receiving an instruction manipulation such as force-quit, whereby practice can be stopped during the procedure.

Figure 8:
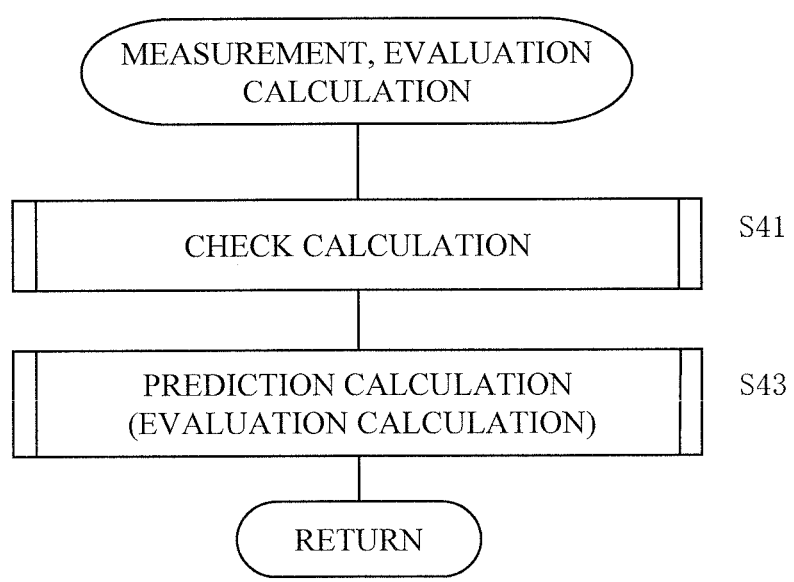
FIG. 8 is a flowchart showing one embodiment of the measurement and evaluation calculation processing.

FIG. 8 is a flowchart showing one embodiment of the measurement and evaluation calculation processing at Step S21. In FIG. 8, firstly, calculation for check at the first stage is executed (Step S41), and after affirming the determination at the calculation for check, calculation for prediction at the second stage is executed (Step S43).

Figure 9:
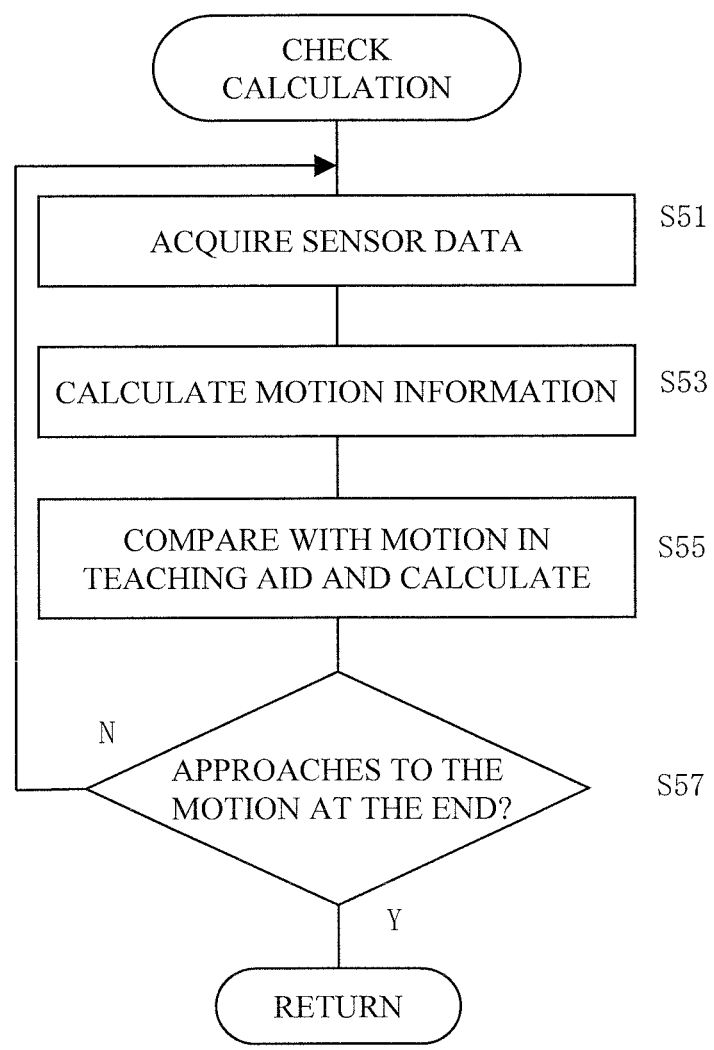
FIG. 9 is a flowchart showing one example of the calculation for check processing.

FIG. 9 is a flowchart showing one example of the calculation for check processing at the first stage. Firstly, sensor data from the motion sensing unit 116 on the forceps 114 manipulated by the learner is acquired (Step S51). Next, parameters of motion information are calculated based on the acquired sensor data (Step S53). Subsequently, a variation state of a difference or the like in the parameters between the motion information calculated and the motion information on the model person is monitored (Step S55), whereby determination is made whether the manipulation of the forceps by the learner approaches or not the motion at final part of the teaching-aid video in the current segment (Step S57). Then, if the manipulation is determined to approach the motion corresponding to the motion at the final part, return is executed. On the contrary, if it is not determined to approach the motion corresponding to the motion at the final part, the procedure returns to Step S51, and similar check processing is repeated. During the repeat processing returning from Step S57 to Step S51, if manipulation of the manipulation unit 121 occurs as interruption, the procedure is configured to shift to Step S29.

Figure 10:
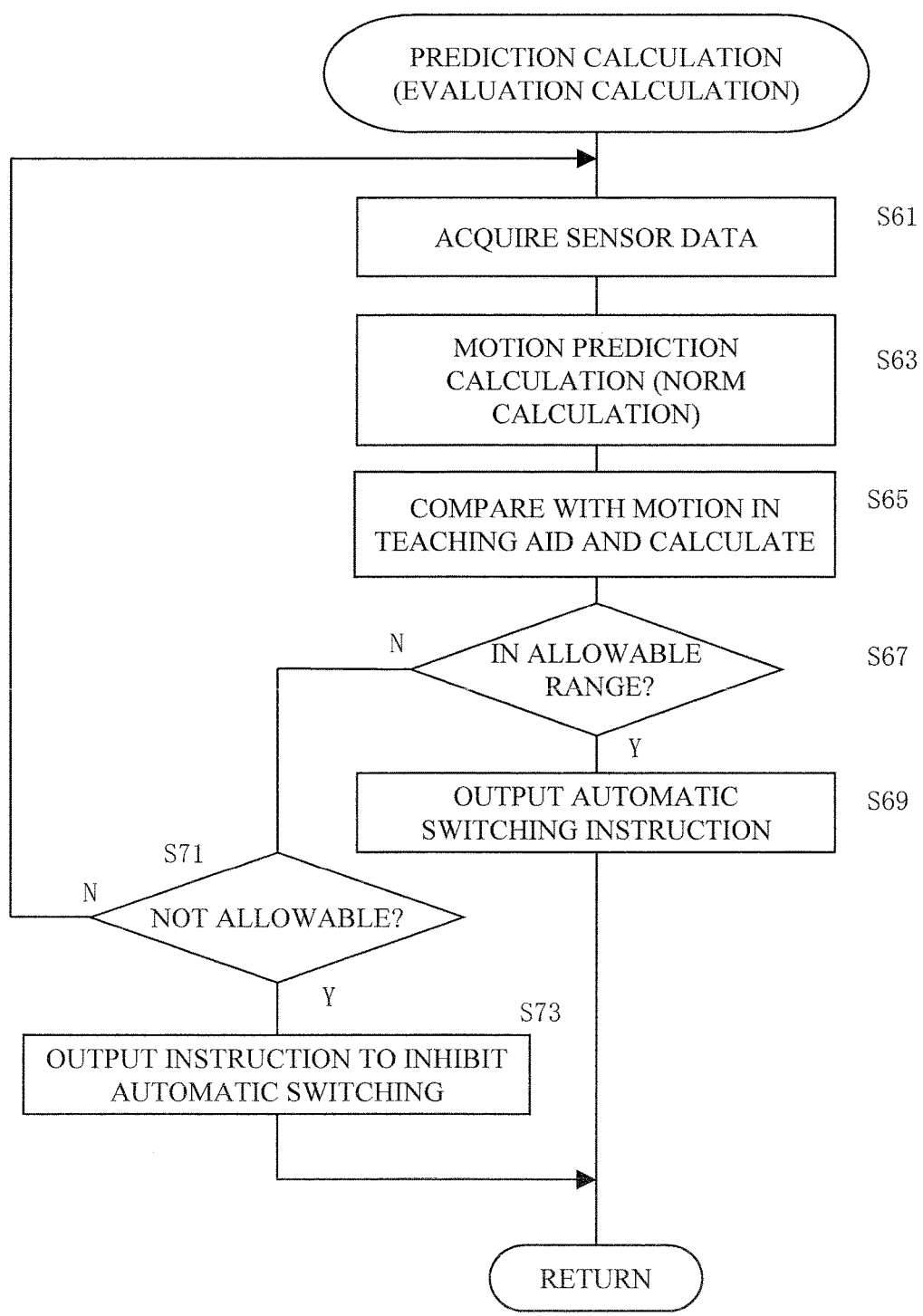
FIG. 10 is a flowchart showing one example of the calculation for prediction processing.

FIG. 10 is a flowchart showing one example of the calculation for prediction processing at the second stage. Firstly, sensor data from the motion sensing unit 116 on the forceps 114 manipulated by the learner is acquired (Step S61). Next, parameters of motion information are calculated based on the acquired sensor data, and motion prediction calculation is executed to calculate norm (Step S63). Subsequently parameters calculated on both sides are compared, and norms on both sides are compared (Step S65). For instance, under the condition that a difference between parameters of both sides is within a certain range, determination is made whether the difference in norm between both sides is within a threshold range or not (Step S67). If it is within an allowable range, an instruction of automatic switching is output (Step S69). On the contrary, if it is determined as not within in the allowable range at Step S67, a next determination is made whether it is within a not-allowable range or not (Step S71). If it is not within a not-allowable range, the procedure returns to Step S61, and similar prediction processing is repeated. On the contrary, if it is within a not-allowable range, an instruction to inhibit automatic switching is output (Step S73). Steps S71 and S73 may be omitted, and during the repeat processing returning from Step S67 to Step S61, if manipulation of the manipulation unit 121 occurs as interruption, the procedure may be configured to shift to Step S29.

Figure 11:
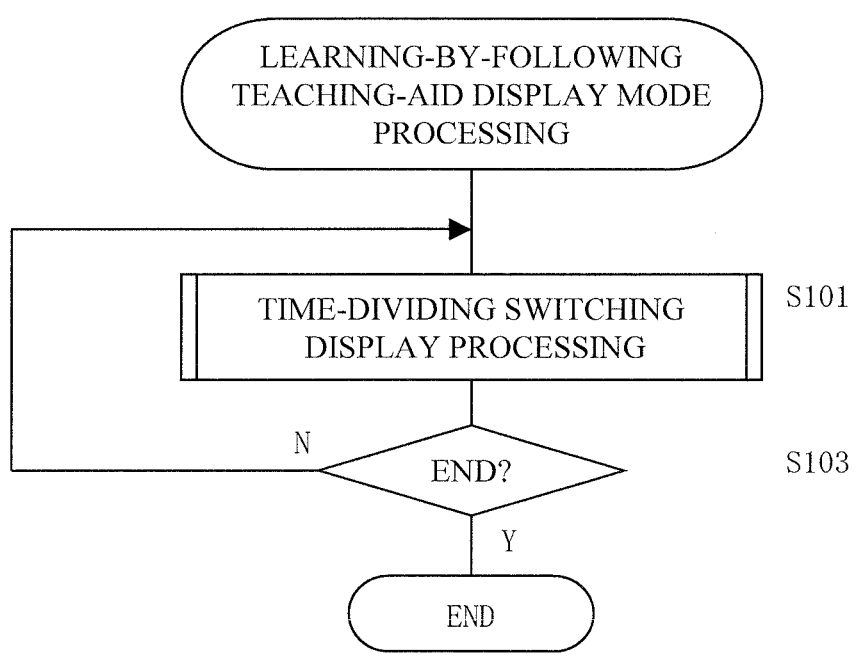
FIG. 11 is a flowchart showing one embodiment of the learning-by-following teaching-aid display mode processing.

FIG. 11 is a flowchart showing one embodiment of the learning-by-following teaching-aid display mode processing. In this flowchart, time-dividing switching display processing is executed (Step S101). This time-dividing switching display processing also can be executed the desired number of times as the learner intends, i.e., in response to an instruction manipulation of the manipulation unit 121, and may be finished (Step S103).

Figure 12:
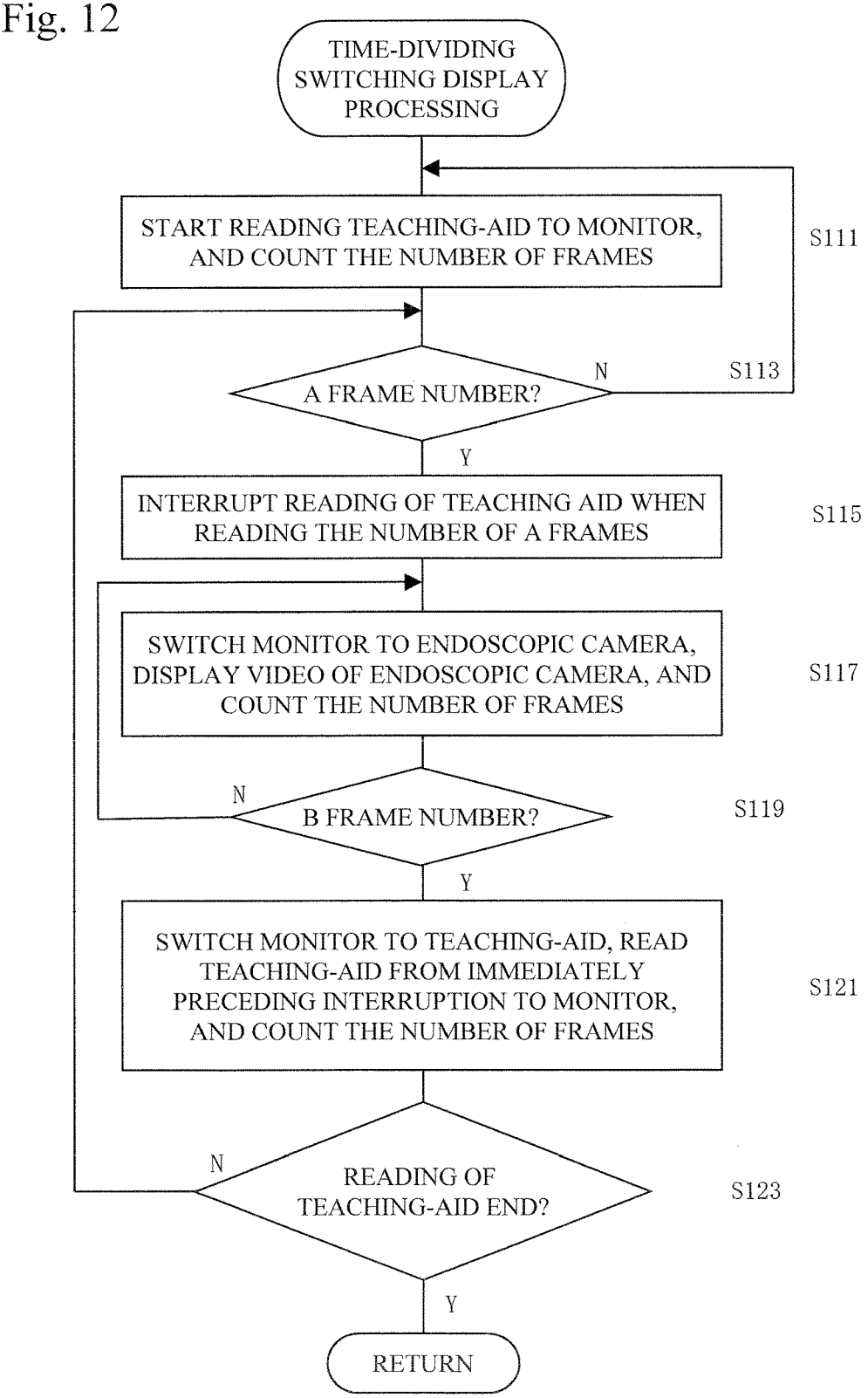
FIG. 12 is a flowchart showing one embodiment of the time-dividing switching display processing in the learning-by-following teaching-aid display mode processing.

FIG. 12 is a flowchart showing one embodiment of the time-dividing switching display processing in the learning-by-following teaching-aid display mode processing. Firstly, a teaching-aid video is read from the learning-by-following teaching-aid storage unit 231 and is output to the monitor 13, and processing to count the number of frames is performed (Step S111). Next, after the video corresponding to the number of A frames is displayed (Yes at Step S113), reading of the teaching aid is interrupted at the time of reading the number of A frames (Step S115).

Subsequently, the display on the monitor 13 is switched to the endoscopic camera 115, live video taken with the endoscopic camera 115 is displayed on the monitor 13, and processing to count the number of frames is performed (Step S117). Next, after the video corresponding to the number of B frames is displayed (Yes at Step S119), the display on the monitor 13 is switched to the teaching aid, and the teaching-aid video in the learning-by-following teaching-aid storage unit 231 and from the address in which interruption occurred immediately before is output to the monitor 13, and the number of frames is counted (Step S121). Next, determination is made whether reading of the teaching-aid video ends or not (Step S123), and if the reading of the teaching-aid video does not end, the procedure returns to Step S113, where the processing to alternately display the teaching-aid video corresponding to the number of A frames and the live video taken with the endoscopic camera corresponding to the number of B frames on the monitor 13 is repeated. On the contrary, if the reading of the teaching-aid video ends, the present flow ends.

Herein in the time-dividing switching display processing, A frames are read at one time from the learning-by-following teaching-aid storage unit 231 (Yes at Step S113), and in another embodiment, video frames may be continuously read from the learning-by-following teaching-aid storage unit 231, but they are not introduced to the monitor 13 while the live video taken with the endoscopic camera 115 is displayed, or even when they are introduced, they may not be displayed in another embodiment. Thereby, a change in the time direction of video frames from the learning-by-following teaching-aid storage unit 231 can match with the actual time.

The present invention may have the following embodiments.

(1) The present embodiment describes the example of a suture ligature procedure, which is not a limiting example, and the present invention is applicable to a special medical procedure using an endoscopic camera as well. The present invention is applicable to various types of medical procedures in telesurgery as well that are performed using a surgical robot while observing the image of a diseased part via a monitor in a remote location, because the number of specialists who can handle the robot is small.

(2) The applicable range of the present invention is not limited to a medical field, which is applicable to other fields as well. For instance, they include a field requiring the skill or the techniques, e.g., the field of pottery art, because they have various motion elements corresponding to the creation process of a product (work), and a product or the like is completed through these motion elements so that a series of motions are finished. The present invention is applicable to a teaching aid of cooking practice as well, in which preparation specific to each food is performed, and food to be intended is completed finally. It is applicable to various types of training in sports as well.

(3) The present embodiment is configured so that the monitor 13 is disposed in front of a learner, and in another embodiment, a video see-through head mounted display (VST-HMD) that is a device to realize a visual guidance of a physical motion may be used as the monitor.

(4) When the video taken with the endoscopic camera 115 is introduced to the monitor 13, delaying processing may be performed so that a predetermined time lag is set by the information processor 20, whereby a sense of force can be given to the learner, and more realistic learning can be expected. A digital filter to perform differential processing on the video may be intervened in the information processor 20, whereby edge enhancement of the video can be achieved, and the video can be recognized better.

(5) In the present embodiment, switching from the procedure learning to the learning-by-following is performed through an instruction to the manipulation unit 121. Instead, shifting to the learning-by-following may be performed automatically after a certain time elapsed from the ending of the procedure learning. As the condition to shift to the learning-by-following, the shifting may be limited to the case where all of the teaching-aid video segments are viewed through automatic switching instructions during the procedure learning.

(6) In addition to the motion sensing unit 116, motions of the learner and the forceps may be evaluated about the fluidity or smoothness, for example, by attaching a pressure sensor to the finger insertion parts on the proximal end to measure the finger pressure so as to measure the degree of force when the fingers are moved, or by attaching a myoelectric sensor (electrode plate, for example) at an appropriate position of the learner, such as at an arm, so as to measure myoelectric potential generated during the movement.

(7) The present embodiment is configured so that the practice video and the static image of the final frame of the teaching-aid video segment reproduced immediately before are displayed together on the monitor 13, which is not a limiting example. The position (the direction as needed) where the video of the target for manipulation, in the present example, the tip end of the video 1141 of the forceps, is to reach finally in the segment may be indicated with a marker as a point. Alternatively, practice video only may be displayed without performing alongside-displaying, and for example, guidance with voice only may be used.

(8) Displaying of the final video frame may be started at the time when the display on the monitor 13 is switched to the endoscopic camera 115, or may start in association with a predetermined condition, for example, the progress of the learner's practice. As a method for associating it with the progress of the learner's practice, an alongside-displaying timing may be set in a predetermined range wider than that for the determination at the first stage (Step S57) to calculate for checking, for example.

(9) The training-aid video displayed alongside may be a static image as well as a moving image. For instance, the video in about a few seconds at the end of the teaching-aid video segment may be reproduced repeatedly in another embodiment.

(10) In the present embodiment as stated above, evaluation is made in two stages at the measurement and evaluation calculation processing by the evaluation unit 216, and only one of the first and the second stages may be performed. The above describes the comparison processing of parameters and the norm comparison processing, and these evaluations are as follows. That is, they are switched desirably mainly in the state where positional error vector $\Delta P$ of the position of the portion to be measured between the training-aid video and the actual video is aligned in the substantially same direction with the speed vector v when the teaching-aid video starts to move, while waiting for the timing when $v \approx \Delta P/T$, where T denotes the switching period. If the situation is deviated greatly from this condition, the effect of promoting learning due to illusion of the motion connection will be greatly degraded.

(11) For this switching, the switching period and the phase pattern that bring the blending feeling as indicated in the prior art (patent application No. 2012-97328) are used for the timing to switch into the teaching-aid video segment, whereby the effect of promoting illusion effect can be expected. For instance, when positional error vector ΔP is small to some extent at the time of connection, i.e., when their positions are closer, the blinking period, i.e., the switching period may be switched to the pattern of blending feeling. Herein the blending feeling pattern is preferably the frequency of 2 Hz to 4 Hz, and the self/other ratio is 1:1 to 1:3.

As described above, a motion learning support apparatus according to the present invention preferably includes: a first learning support processor configured to display a teaching-aid video segment and a segment of practice video of a learner alternately on a monitor, the teaching-aid video segment being obtained by dividing teaching-aid video on a motion in a time direction, and the practice video being of the learner who is imitating a motion of the teaching-aid video segment and being taken with an imaging unit; a motion sensor configured to detect a motion of the learner; and an evaluation unit configured to evaluate similarity of a motion of the learner to a motion in the teaching-aid video segment, and the first learning support processor is configured to, when the evaluation unit evaluates that the motions are similar, switch the monitor from video taken with the imaging unit to a following teaching-aid video segment. With this configuration, if the motion of the learner is similar to the motion in the teaching-aid video segment, i.e., if they are brought closer, the video is switched in a timely manner so that the motion in the video of the learner can lead to the following teaching-aid video segment, whereby the learner has an illusion as if they started a motion of the next segment similarly to that of the model person, and can have a memory thereof as a more vivid and specific behavior image, so that the learning effect therefrom can be more improved.

In the motion learning support apparatus according to the present invention, the first learning support processor preferably is configured to display, during displaying video taken with the imaging unit on the monitor, video at an end of the teaching-aid video segment reproduced immediately before together. With this configuration, since the teaching-aid video at the end is displayed, the learner can easily recognize the reaching position.

In the motion learning support apparatus according to the present invention, the first learning support processor preferably is configured to display video taken with the imaging unit and video at a final part of the teaching-aid video segment reproduced immediately before in a view synthesis method. With this configuration, since the reaching position is displayed so as to match with the perspective of the learner, whereby the illusion as stated above is induced when the position and the timing are correct, so that the learner can have a memory of the motion as a more vivid and specific behavior image, and the learning effect therefrom can be more improved.

In the motion learning support apparatus according to the present invention, the first learning support processor preferably is configured to display video at the final part of the teaching-aid video segment reproduced immediately before in a display format different from a display format of video taken with the imaging unit. With this configuration, the learner can easily distinguish their own live video from the teaching-aid video segment.

In the motion learning support apparatus according to the present invention, the first learning support processor preferably is configured to display video at the final part of the teaching-aid video segment reproduced immediately before while letting it blinking. With this configuration, the learner can easily distinguish their own live video from the teaching-aid video segment.

In the motion learning support apparatus according to the present invention, the first learning support processor preferably is configured to display video a the final part of the teaching-aid video segment reproduced immediately before from a predetermined time of the practice video being displayed. With this configuration, since the reaching position at the final part of the segment is shown from the beginning of learning, manipulation can be made stable as compared with the case of starting the display from the middle of the learning, and so the learning effect can be enhanced.

In the motion learning support apparatus according to the present invention, video at the final part of the teaching-aid video segment reproduced immediately before preferably is a static image. With this configuration, since the teaching-aid video segment is still, the learner can easily distinguish their own live video therefrom.

Preferably the motion learning support apparatus according to the present invention further includes a second learning support processor configured to display the teaching-aid video before dividing and video taken with the imaging unit on the monitor in a time-dividing synthesis manner. With this configuration, the effect of inducing a motion can be exerted, and the learning efficiency can be improve.

Preferably, a method for supporting motion learning according to the present invention includes: a display step of displaying a teaching-aid video segment and a segment of practice video of a learner alternately on a monitor, the teaching-aid video segment being obtained by dividing teaching-aid video on a motion in a time direction, and the practice video being of the learner who is imitating a motion of the teaching-aid video segment and being taken with an imaging unit; an evaluation step of detecting a motion of the learner in the display step, and evaluating similarity of a motion of the learner to a motion in the teaching-aid video segment; and a switching step of, when it is evaluated that the motions are similar, switching the monitor from video taken with the imaging unit to a following teaching-aid video segment. With this configuration, if the motion of the learner is similar to the motion in the teaching-aid video segment, i.e., if they are brought closer, the video is switched in a timely manner so that the motion in the video of the learner can lead to the following teaching-aid video segment, whereby the learner has an illusion as if they started a motion of the next segment similarly to that of the model person, and can have a memory thereof as a more vivid and specific behavior image, so that the learning effect therefrom can be more improved.

In the method for supporting motion learning according to the present invention, in display step, during displaying video taken with the imaging unit on the monitor, video at a final part of the teaching-aid video segment reproduced immediately before preferably s displayed alongside. With this configuration, since the teaching-aid video at the end is displayed, the learner can easily recognize the reaching position.

REFERENCE SIGNS LIST

1 Motion learning support apparatus
10 Device for practicing
114 Forceps
115 Endoscopic camera (imaging unit)

116 Motion sensing unit (motion sensor)
121 Manipulation unit
13 Monitor
20 Information processor
21 Controller
211 Procedure learning video creation unit
212 Procedure learning video display processing unit (first learning support processor)
213 Learning-by-following video display processing unit (second learning support processor)
215 Motion information acquisition unit (motion sensor)
216 Evaluation unit
232 Procedure learning teaching-aid storage unit

The invention claimed is:

1. A motion learning support apparatus for laparoscopic surgery training, comprising:
a dry box that imitates a patient's body;
a base on which the dry box is placed;
a motion detection unit;
a monitor that displays an image; and
an information processing device,
wherein the dry box comprises:
a tubular body imitating an abdomen of the patient's body;
a laparoscopic camera; and
a forceps,
wherein, on the upper surface of the tubular body, a plurality of circular holes are provided on membranes having cross-shaped cuttings for inserting and removing the forceps and the laparoscopic camera;
wherein the laparoscopic camera is fixed to the dry box and captures movement of a tip of the forceps of a model person and a learner for suturing;
wherein the motion detection unit comprises:
a magnetic generator attached to the base; and
magnetic sensors attached in three axial directions at predetermined positions of the forceps;
wherein the motion detection unit detects motion information including a position, orientation, and displacement speed of the tip of the forceps;
wherein the information processing device comprises:
an operation unit;
a RAM;
a ROM; and
a control unit;
wherein the operation unit accepts instructions including teaching-aid display mode switching input by the learner;
wherein the RAM comprises:
a learning-by-following teaching-aid storage unit for storing an image of movement of a tip of the forceps of the model person; and
a procedure learning teaching-aid storage unit for storing segments of a teaching-aid video obtained by dividing the image of the movement of the tip of the forceps of the model person;
wherein the control unit, when a program stored in the ROM is executed, functions as an evaluation unit, a procedure learning video display processing unit, and a learning-by-following video display processing unit;
wherein the evaluating unit calculates a difference between the motion information of the tip of the forceps of the learner detected by the motion detection unit at a time point corresponding to just before an end of one segment of the teaching-aid video and the motion information of the tip of the forceps of the model person at a time point immediately after a start of a next segment of the teaching-aid video, and evaluates as to whether or not the difference is within a predetermined threshold value;
wherein the procedure learning video display processing unit replays one segment of the teaching-aid video in response to an instruction from the learner in procedural learning mode, and whenever the replay is completed, switches an image on the monitor to an image of the laparoscopic camera capturing the movement of the tip of the forceps of the learner; then, if evaluation result by the evaluation unit is within the predetermined threshold value, automatically switches the image on the monitor to the next segment of the teaching-aid video; and, if the evaluation result is larger than the predetermined threshold value, waits for an instruction from the learner to display the next segment of the teaching-aid video; and
wherein the learning-by-following video display processing unit, in response to an instruction from the learner in learning-by-following mode, time-divisionally displays the teaching-aid video of the learning-by-following teaching-aid storage unit and the image of the laparoscopic camera of the learner, from a same viewpoint and in frequency of approximately 2 Hz to 4 Hz and in the learner-to-the model person ratio from 1:1 to 1:3 alternately.

2. The motion learning support apparatus according to claim 1, wherein, in place of the magnetic generator and the magnetic sensors of the motion detection unit, a three-dimensional acceleration sensor is provided at the tip of the forceps.

3. The motion learning support apparatus according to claim 1, wherein, in place of the motion information including a position, orientation, and displacement speed of the tip of the forceps detected by the magnetic generator and the magnetic sensors of the motion detection unit, a motion information including a position, orientation, and displacement speed of the tip of the forceps calculated from an image captured by the laparoscopic camera are used.

4. The motion learning support apparatus according to claim 2, wherein the motion detection unit detects displacement acceleration in addition to the position, the orientation, and the displacement speed of the tip of the forceps.

5. The motion learning support apparatus according to claim 3, wherein the motion detection unit detects displacement acceleration in addition to the position, the orientation, and the displacement speed of the tip of the forceps.

* * * * *